(12) United States Patent
Wei

(10) Patent No.: US 7,417,048 B2
(45) Date of Patent: Aug. 26, 2008

(54) ARYL-SUBSTITUTED DERIVATIVES OF CYCLOALKYL AND BRANCHED CHAIN ALKYL CARBOXYLIC ACIDS USEFUL AS ANTINOCICEPTIVE DRUGS FOR PERIPHERAL TARGETS

(76) Inventor: Edward T. Wei, 480 Grizzly Peak Blvd., Berkeley, CA (US) 94708

( * ) Notice: Subject to any disclaimer, the term of this patent is extended or adjusted under 35 U.S.C. 154(b) by 567 days.

(21) Appl. No.: 11/025,547

(22) Filed: Dec. 28, 2004

(65) Prior Publication Data
US 2005/0159394 A1  Jul. 21, 2005

Related U.S. Application Data

(60) Provisional application No. 60/534,024, filed on Dec. 31, 2003.

(51) Int. Cl.
*A01N 43/54* (2006.01)
*A61K 31/505* (2006.01)
*C07D 239/02* (2006.01)

(52) U.S. Cl. ........................ 514/275; 544/297
(58) Field of Classification Search ............. 514/275; 544/297
See application file for complete search history.

(56) References Cited

U.S. PATENT DOCUMENTS

| 4,193,936 | A | 3/1980 | Watson et al. |
| 4,318,900 | A | 3/1982 | Rowsell et al. |
| 5,009,893 | A | 4/1991 | Cherukuri et al. |
| 5,244,670 | A | 9/1993 | Upson et al. |
| 5,698,181 | A | 12/1997 | Luo et al. |
| 6,497,859 | B1 | 12/2002 | Zanone et al. |
| 6,784,266 | B2 * | 8/2004 | Kim et al. .................. 526/259 |

FOREIGN PATENT DOCUMENTS

GB  1457671  12/1976

\* cited by examiner

*Primary Examiner*—James O. Wilson
*Assistant Examiner*—Erich A Leeser

(57) ABSTRACT

Novel peripheral antinociceptive compounds are disclosed having a pharmacophore unit that target small-diameter nerve fibers that transmit signals of pain and discomfort from the soma and viscera. By acting on this target, the pharmacophore unit obtunds pain and diminishes hyper-reflexia from organs such as the skin, the respiratory tract, the corpus, the lower urinary tract, and the bowel. The pharmacophore unit is coupled to substituents that facilitate delivery of the pharmacophore to its target.

6 Claims, 1 Drawing Sheet

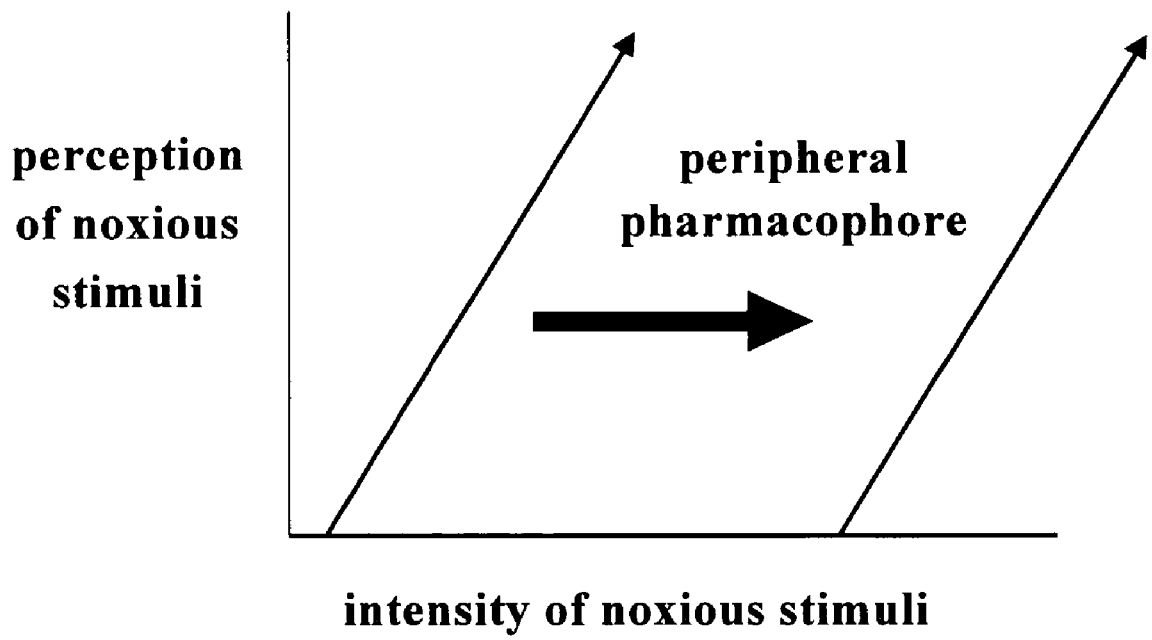

ARYL-SUBSTITUTED DERIVATIVES OF CYCLOALKYL AND BRANCHED CHAIN ALKYL CARBOXYLIC ACIDS USEFUL AS ANTINOCICEPTIVE DRUGS FOR PERIPHERAL TARGETS

CROSS-REFERENCE TO RELATED APPLICATIONS

This application claims benefits of U.S. Provisional Application No. 60/534,024, "Antinociceptive Drugs for Peripheral Targets" filed on Dec. 31, 2003.

BACKGROUND OF THE DISCLOSURE

1. Field of the disclosure

The field of art of this disclosure generally concerns chemicals designed to act as peripheral antinociceptive drugs. By "peripheral", I mean that the target of the drug action is located outside the central nervous system, that is, outside of the brain and spinal cord. By "antinociceptive", I mean that the drug suppresses the perception of noxious stimuli. The compounds described are aryl-substituted derivatives of cycloalkyl and branched chain alkyl carboxamides and carboxylic acids useful in treating clinical disorders such as itch, pain, and sensory discomforts from breathing disorders, lower urinary tract disorders, bowel dysfunction and as insect repellents.

2. Description of Related Art

There are currently two major classes of drugs that act peripherally to attenuate transmission of nociceptive signals to the central nervous system. One class of drugs are the local anesthetics, such as procaine and lidocaine, which act on peripheral nerve fibers to inhibit conduction of noxious signals towards the central nervous system. Another class of drugs are agents like aspirin and ibuprofen which inhibit the synthesis of certain prostaglandins. These prostaglandins when released by tissues during injury or inflammation lower the threshold of firing of sensory nerve fibers that respond to noxious stimuli. A third group of drugs, the narcotic analgesics, are effective in the suppression of pain, but they act within the brain and the spinal cord.

Local anesthetic compounds are not active orally and must be infiltrated into tissues containing the target nerve fibers. The aspirin/non-steroidal anti-inflammatory compounds (NSAID and thenarcotic analgesics) are effective drugs but the NSAIDs may produce gastric ulceration and kidney failure and the narcotics have side-effects such as respiratory depression, tolerance and dependence. The NSAIDs reduce inflammatory pain, but are not effective against neuropathic or visceral pain. The treatment of neuropathic pain is especially complex, with empirical use of agents such as amitriptyline, clonazepam, clonidine, carbamazepine and gabapentin.

Pain, defined by Sir Charles Sherrington as "the psychic adjunct of an imperative protective reflex", is activated by increased discharge of small-diameter sensory fibers. Anatomically, these fibers are called unmyclinated C fibers and thinly myelinated Aδ fibers. Functionally, these fibers are also called polymodal and may contain in one group neuropeptides such as calcitonin-gene related peptide and substance P, or in another group contain phosphatases and binding sites for isolectin B4. These sensory fibers also contain various receptors, including the transient potential receptor (TRP) potential family of receptors that code for thermosensation and pain. Pain is categorized as nociceptive or neuropathic, the first caused by tissue injury and the latter caused by direct damage to the nerve fiber. There are many conditions that produce pain, for example, acute pain after tissue trauma, chronic pain from osteoarthritis, cancer pain, and neuropathic pain, for example, associated with end-stage renal diseases and with diabetes mellitus. Other related sensory disorders arising from polymodal neuronal elements are pruritus, for example from uremia, cholestasis, various forms of dermatitis, polycythemia vera, hyperthyroidism, lymphoma, and human immunodeficiency (HIV) virus infections; and sensations from the nasal membranes, for example, the urge to sneeze; and sensations from the upper airways, for example, the urge to cough.

Another form of sensory fiber disorder is visceral hypersensitivity or hyper-reflexia. Urinary incontinence (UI) is defined as the involuntary loss of urine that can be demonstrated objectively and which constitutes a social or hygienic problem. UI occurs when the pressure within the bladder exceeds that within the urethra during the filling phase. Overactive bladder (OA) and urge incontinence is a type of UI that is associated with a strong desire to urinate and correlates with an overactive detrusor muscle. Urge incontinence is usually recognized by the abrupt sensation that urination is imminent and can occur even when the bladder is virtually empty.

It is estimated that OA affects more 17 million Americans, making it more prevalent than, for example, asthma, osteoporosis, diabetes mellitus or Alzheimer's disease. OA with urge incontinence is a problem in older men with bladder irritation from benign prostate hypertrophy (BPH), a condition which obstructs urine passage. In women, stress incontinence, a sub-category of UI, arises as a defect in the urethral closure mechanism caused, for example, by physical damage to muscle and nerves on the pelvic floor, bladder neck, or urethra during childbirth. Sufferers of stress incontinence have leak of small volumes of urine after actions such as laughing, coughing, sneezing, lifting, jumping and running, all of which produce abrupt increases in intra-abdominal pressure. Stress incontinence is estimated to affect approximately 25% of women with urinary incontinence and surgery is the most effective treatment with a cure rate of 75 to 85%. Other conditions that may produce OA are lower urinary tract infections and chronic inflammation, such interstitial cystitis.

Pharmacotherapy is currently the principal treatment for OA. Selective antimuscarinic drugs, such as oxybutynin and tolterodine, designed to inhibit smooth muscle contraction in the detusor, are administered to reduce the frequency of uncontrolled contractions and of voiding. These drugs are claimed to be effective in about 60% of the patient population, but longterm compliance is low, possibly because of side-effects of these drugs such as dry mouth. Another agent is phenazopyridine, an azo dye that is thought to act as an urinary anesthetic. This compound, however, can cause methemoglobinemia, turns the urine to a yellow-orange to red color, and produces adenocarcinomas (cancers) in experimental animals. Intravesical instillation of vanilloid agonists, such as capsaicin and resinerferatoxin, is also used as an experimental form of treating OA, but the chemicals are difficult to administer and causes severe irritation as a side-effect.

Like the bladder, the gut is a complex organ with its own enteric nervous system. The simplified "brain" of the gut has about 100 million neurons. The efferent nerves regulate secretion by intestinal glands and control peristalsis. Sensory afferent nerves (Aδ and C) fibers located in the gut respond to thermal and nociceptive signals. The lining of the gut has high metabolic activity and a turnover rate of about 5 days, that is, within a period of 5 days, the entire lining is shed and renewed. This is a turnover of about ¼ pounds of cells per day. Injury to the intestinal mucosa from exposure to chemical agents such as anticancer drugs, from inflammatory responses, and from autoimmune diseases, from infections, or from physical injuries such as radiation or trauma, disrupt the enteric nervous system and contribute to symptoms and signs such as pain, a sense of distension, changes in the frequency of bowel movements, intra-luminal bleeding, and flatulence.

Irritable bowel syndrome (IBS) is a common disorder characterized by abdominal pain in the setting of altered perception of viscerosensory stimuli. This so-called visceral hyperalgesia (or hypersensitivity) occurs in the absence of detectable organic disease in the peripheral organs and may cause normal or physiologic contractions to be perceived as painful. Although the pathogenesis of IBS remains speculative and is probably multifactorial, a prevailing paradigm is that transient noxious events lead to long-lasting sensitization of the neural pain circuit, despite complete resolution of the initiating event. A similar situation exists in inflammatory bowel disease (IBD), the two principal conditions being Crohn's disease and ulcerative colitis. In IBD there is clear evidence of organ histopathology and the symptoms and signs of pain and discomfort are present to a greater extent, sometimes requiring surgical removal of the lower bowel. Currently pharmacological treatment of IBS includes tegaserod (Zelnorm®), a selective 5-hydroxytrptamine receptor agonist, designed to overcome the constipation-predominant type of IBS. For IBD treatment, a prodrug, sulfaslazine, or 5-aminosalicylic acid is used. These drugs modulate the IBD processes in the gut.

Proctitis is inflammation of the lining of the rectum. Proctitis can be short term (acute) or long term (chronic). Proctitis has many causes. It may be a side effect of autoimmune diseases of the lower bowel, such as ulcerative colitis and Crohn's disease. Sexually transmitted diseases may cause proctitis. Proctitis is frequently a side-effect of radiation used to treat prostate cancer or cancer of the female organs. The rectum resides just behind the prostate in the male and the vagina and uterus in the female, so when these organs are irradiated, the bowel wall is injured. Radiation proctitis is manifested as the new growth of many tiny blood vessels on the epithelial surface of the rectum. These blood vessels are fragile and bleed with minimal trauma, resulting in blood in the stool. If the bleeding is severe, anemia or a low red cell blood count can occur. Other causes of proctitis include traumatic rectal injury, allergies, and malfunction of the nerves in the rectum. Patients infected with human immunodeficiency virus or receiving immunosuppressive drugs are especially susceptible to infectious agents attacking the lower gut lining and surrounding tissues.

The most common manifestation of proctitis is a frequent or continuous sensation of an urge to have a bowel movement. This distressing but ineffectual urge to empty the rectum is called tenesmus. Other symptoms include constipation, a feeling of rectal fillness, left-sided abdominal pain, passage of mucus through the rectum, rectal bleeding, and anorectal pain. Proctitis because it leads to bleeding, some incontinence, and inflammation will produce subjective discomfort, pain, and itch in the entire anorectal area.

The surfaces of the upper airways (nose, pharynx, bronchi and bronchioles) are densely innervated and any inflammation or altered airflow quickly generates sensations of itch, irritation, obstruction, choking, air hunger, suffocation and subjective discomfort. The sensory nerves that mediate the sensations of breathing disorders are also the target of the drugs of this invention; the therapeutic goal being to provide refreshed breathing, less sneezing and coughing, decreased inspiratory effort, and relief of dyspnea.

I have previously described the use of certain compounds to treat itch or pain. Thus, U.S. patent application, publication No. 2003/0207851, published Nov. 6, 2003, titled "Therapeutic 1,2,3,6-tetrahydropyrimidine-2-one compositions and methods therewith" describes a therapeutic composition that comprises a 1-R1-phenyl, 4R2-phenyl substituted 1,2,3,6-tetrahydropyrimidine-2-one cold receptor agonist in a therapeutically effective amount. A particularly preferred cold receptor agonist embodiment is called "icilin" and a particularly preferred composition has icilin dispersed as an emulsion in a dermatologically acceptable vehicle. Icilin, formulated and administered as a liniment, and preferably in combination with one or more pharmaceutically active drugs, offers improved therapeutic benefit for the treatment of pruritus.

Watson et al. N-Substituted Paramenthane Carboxamides, U.S. Pat. No. 4,193,936, Mar. 18, 1980 and Rowsell et al., Alicyclic Amides Having a Physiological Cooling Effect, U.S. Pat. No. 4,318,900, Mar. 9, 1982, disclosed compounds with physiological cooling effects. Various uses of the Watson et al. and Rowsell et al. compounds are noted in several subsequent patents: Cherukuri et al., U.S. Pat. No. 5,009,893, Apr. 23, 1991; Upson et al. U.S. Pat. No. 5,244,670, Sep. 14, 1993; Luo, U.S. Pat. No. 5,698,181, Dec. 16, 1997; and Zanone et al., U.S. Pat. No. 6,497,859, Dec. 24, 2002. These compounds are also claimed for use as an insect repellent in Gautschi et al., WO 02/15692 A1, Feb. 28, 2002.

BRIEF DESCRIPTION OF THE DRAWING

FIG. 1 graphically illustrates a functional shift towards an elevated threshold for the perception of noxious stimuli with a peripheral anitinociceptive drug.

DETAILED DESCRIPTION

I describe here a new class of drugs designed to act on peripheral targets to elevate the sensory threshold for noxious stimuli. The precise molecular and neurophysiological mechanisms of action of these agents are not known, but empirically these agents produce a dose-dependent elevation in the threshold for perception of noxious stimuli, as illustrated in FIG. 1. The perception is directly linked to the activity of the polymodal sensory nerve fibers. Thus, in the presence of the peripheral antinociceptive drug there is a functional shift towards an elevated threshold for the perception of noxious stimuli.

Introduction. Without being bound by theory, I believe that the compounds described here act on peripheral small sensory nerve (polymodal) fibers to inhibit, counteract, mask, attenuate or otherwise reduce the activation, transmission, or integration of neuronal signals for somatic and visceral pain. Included in this antinociceptive action is an inhibition of hypersensitivity in airways and in viscera such as the bladder and lower intestinal tract. Compounds of this discovery have a pharmacophore unit that is coupled to certain groups such as a sulfonyl or a carbonyl group. The coupling of the antinociceptive pharmacophore to such a group facilitates delivery of pharmacophore to the biological target.

I will sometimes describe compounds of this discovery by using the phrase "peripheral antinociceptive pharmacophore"; the pharmacophore constitutes functional groups on the molecule necessary to activate the receptors while certain groups, shown as -Z-R" in Formulas 1 and 2, facilite delivery of pharmacophore to the biological target These compounds are believed to be novel and are shown in Formula 1 and Formula 2. They are aryl-substituted derivatives of cycloalkyl- and branched chain alkyl carboxamides and carboxylic acids:

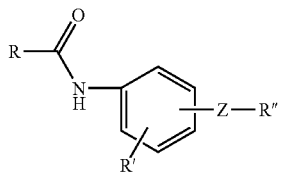

Formula 1

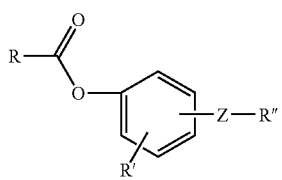

Formula 2

Thus, novel compounds of Formulas 1 and 2 are:

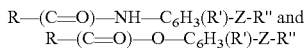

where R is a saturated or monoethylenically unsaturated alkyl-substituted cyclic or bicyclic alkyl radical containing a total of 7-14 carbon atoms and is selected from the group cyclopentanes, cyclohexanes, cycloheptanes, cyclooctanes, cyclononanes, [3.1.1]bicyclo-heptanes and -hept-5-enes, [2.2.1]bicyclo-heptanes and -hept-5-enes, and [2.2.2]bicyclo-octanes and -oct-5-enes, each alkyl radical containing from 1 to 3 $C_1$-$C_5$ normal or branched alkyl substituents, which may be the same or different, and where R' is selected from the group hydrogen, hydroxyl, $C_1$-$C_3$ alky, $C_1$-$C_3$ alkoxy, trifluoromethyl, nitro, cyano, halo, and where Z is a divalent oxygenated moiety selected from the group —$SO_2$—, —SO—, or —CO—, and where R" is a monovalent radical selected from the groups —$NHR_1$, or —$NR_1R_2$, or —$OR_3$, or —N=N—$R_4$, or —$R_5$, where $R_1$ can be selected from the groups hydrogen, or $C_1$ to $C_5$ alkyl, or $C_1$ to $C_3$ alkoxyl, or $C_2$ to $C_{12}$ alkyl- and cycloalkylcarbonyl, or aryl or substituted aryl, or substituted heterocyclic containing up to 4 heteroatoms, and where $R_2$ is selected from the group $C_1$ to $C_5$ alkyl, and where $R_3$ is selected from the group hydrogen, aryl or substituted aryl, and where $R_4$ is selected from the group benzamide, 2-hydroxybenzamide, salicylic acid, and where $R_5$ is selected from the groups $C_1$ to $C_5$ alkyl, or aryl or substituted aryl.

Preferably, the heterocyclic radical $R_1$ is oxazoyl, thiazoyl, pyrimidinyl, pyridazinyl, 1,2,4-triazinyl, optionally substituted with up to 3 $C_1$ to $C_3$ alkyl groups, or up to 3 $C_1$ to $C_3$ alkoxyl groups.

Preferably, the aryl radical $R_1$ is phenyl optionally substituted with up to 3 $C_1$ to $C_3$ alkyl groups, or up to 3 $C_1$ to $C_3$ alkoxyl groups.

Preferably, $R_1$, $R_2$ and $R_5$ may comprise an alkylene, or alkyl-substituted alkylene chain of up to 20 carbon atoms, optionally interrupted by oxygen atoms, in such a way as to link two R—(C=O)—NH—$C_6H_3$(R')-Z-R" or R—(C=O)—O—$C_6H_3$(R')-Z-R" moieties together as a pharmacophore dimer.

For many applications, the form of a pharmaceutically acceptable salt of the Formula 1 or 2 compound is useful, such as wherein the salt is an alkali or alkaline earth metal salt, an alkyl-substituted ammonium salt, or a quaternary ammonium salt.

The compounds of Formulas 1 and 2, and compositions including the compounds, are particularly contemplated for therapeutic administration. With reference to Formulas 1 and 2, the -Z-R" group facilitates delivery of the pharmacophore unit or moiety to the biological target.

Choice of Substituents on the Pharmacophore Moiety

One group -ZR" is selected from aromatic sulfonyl compounds because of desirable pharmacokinetic considerations of absorption, distribution, metabolism and excretion. In this group, -ZR" has substituents to enable the molecule to have polar anionic characteristics at pH of 4.5 to 7.5. Thus, the preferred pKa of these molecules are in the range of pH 4.5 to 7.5. The pKa of an organic acid is identical to the pH at which the acid exists 50% as the neutral acid and 50% in the anionic form. Thus at physiological pH, molecules in this group will be substantially in the ionic form. Such compounds will be soluble at urinary pH of 5.5 to 7.5 and excreted into urine after oral administration and absorption. Examples of the effects of substituents on pKa for -ZR" equal to —$SO_2$—$R_1$ are shown in the paper by Bell and Roblin, J. Am. Chem Soc. 64: 2905-2917, 1942, and enumerated as: pKa Constants of Selected Sulfonamides; $N_1$-chloroacetylsulfanilamide 3.79, $N_1$-benzoylsulfanilamide 4.57, S-1,2,4-triazole 4.66, S-1,3, 4-thiadiazole 4.77, $N_1$-p-aminobenzoylsulfanilamide 5.20, $N_1$-acetylsulfanilamide 5.38, S-thiadiazole 5.45, S-pyrimidine 6.17, sulfadiazine 6.48, S-oxazole 6.50, S-pyridazine 7.06, sulfathiazole 7.12, sulfapyridine 8.43, and sulfanilamide 10.43, where S=sulfanilamidyl-. Thus, it can be seen that sulfadiazine pKa=6.48 has desirable pharmacokinetic properties at physiological pH, but sulfanilamide pKa=10.43 does not.

Ideally, where -ZR" is equal to —$SO_2$—$R_1$ and pKa is 5 to 7, the sodium or other mineral salt of the compound confers water solubility. The molecule must still have sufficient lipid permeability to penetrate into the epithelia (e.g. 3-cell lumenal layer of the urinary bladder and ureter) to reach the sensory nerve endings. The aqueous solubility data on four sulfonamides—sulfadiazine, sulfamerazine, sulfisomidine, and sulfisoxazole at 37° C. and pH ranging from 5.5 to 7.0 are given in Goodman and Gilman, Pharmacological Basis of Therapeutics, Chpt. 55, pg. 1147, $3^{rd}$ Edition, 1965. The solubilities of these sulfonamides range from 18 to 4700 mg/ml of liquid and are sufficient to exert pharmacological activities from the plasma or the urine.

Sulfadiazine is used as antibiotic for urinary tract infections and its silver salt is also used a topical antibiotic for the treatment of burn wounds. One peripheral antinociceptive compound of this discovery is derived from sulfadiazine as the -ZR" group, and has the structure illustrated by Formula 3. This compound was synthesized and tested at 20 mg/ml on the lips and nasal mucous membranes. A gentle, cooling effect was obtained, on the lips and on breathing sensation, lasting up to 3 hr after application of 1 mg per nostril (at a volume of 0.06 ml in 2 droplets per nostril). The embodiment, coded as CPS-125, also activated the TRP-M8 coolness receptor, but not TRP-A1. The sulfanilamide analog (pKa 10.43) was inactive, the sulfadimethoxine, sulfisoxazole analogs were slightly active, and the sulfameter and sulfamethoxypyridazine analogs had moderate activities (see Examples).

Formula 3

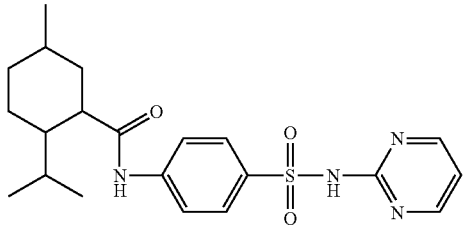

Formula 3 shows the chemical structure of CPS-125 with a peripheral antinociceptive pharmacophore attached to sulfadiazine. The chemical name of CPS-125 is 2-Isopropyl-5-methyl-cyclohexanecarboxylic acid [4-(pyrimidin-2-ylsulfamoyl)-phenyl]-amide. The 2-isopropyl-5-methyl-cyclohexanecarboxylic acid moiety has the chiral properties of levo- or (1R,2S,5R)-(−)-menthol, the preferred steric isomer of menthol for cooling effects and interaction with TRP-receptors.

Still with reference to Formulas 1 and 2, another group, -ZR" is designed so that the molecule is relatively neutral at physiological pH of 7.0 to 7.4. The log octanol/water partition coefficient is designed to be between 2.2 to 4.5. The -ZR" is preferably not aromatic or heterocyclic but designed to contain an alkyl group or a small alkyl with an oxygen atom, and to be relatively resistant to biotransformation by xenobiotic-degrading enzymes in the liver and circulation. Examples are compounds with -ZR" equal to —$SO_2$—$R_1$ and —$CO_2$—$R_1$ wherein —$R_1$ is acetamido or an ethyl ester, respectively, are shown in Formulae 5. The concept here is of a molecule that is lipid permeable and readily absorbed from the gut. After oral administration and entry into the circulation, the compounds reaches sensory nerve endings in inflamed tissues, such as within tumors or in synovial fluid of arthritic joints, and thus be useful for the treatment of pain. Ideally, the molecule, being resistant to degradation, would be active for 24 hours after a single oral dose. For example, in the case of —$CO_2$—$R_1$ wherein —$R_1$ is an ethyl ester, it is estimated that such a compound are relatively resistant to endogenous esterases and will have a half-life in the systemic circulation of at least 3.5 hours. A tert-butyl ester or amide will have an even longer half-life.

A third group, -ZR", for Formulas 1 and 2, is designed for localized delivery to the lower intestinal tract, with minimal systemic absorption. This can be accomplished by making —$R_1$ of a large molecular weight, more hydrophobic, and less water soluble (for example, a phenoxyl group or a glucuronide). Alternatively, -ZR" can be —N=N—$R_4$ and thus designed to be a prodrug, to be released locally in the colon by endogenous bacteria. The molecule is designed for delivery to the lower gastrointestinal tract with the intent of locally reducing sensations of visceral discomfort from the gut lining. Examples of such structures are shown in Formula 5.

In a fourth group, -ZR" may be designed to contain an additional peripheral antinociceptive pharmacophore unit, with optimal 3-dimensional spacing of the pharmacophore units. The purpose here is to increase potency, efficacy, and duration of action. Examples of such template structures are shown in Formula 6.

In the pharmacophores described here, a branched chain hydrocarbon unit is attached to a carbamyl or carbonyl unit and further attached to a substituted aromatic component. Sulfonyl- or carboxyl-groups are familiar entities to pharmacologists and may be used as replacements. For toxicological reasons, a nitro-group is seldom utilized in an orally administered drug.

In the current discovery, novel chemicals are described with a) peripheral antinociceptive pharmacophore unit attached to b) a substituted sulfonamide, sulfonester, sulfone, carboxylester or carboxylamide, mono- or di-valently linked to the aromatic ring; the aromatic substituents being designed to facilitate drug delivery of the pharmacophore to target.

Alternatives to a phenyl ring in Formulas 1 and 2 are a substituted aromatic radical, selected from the group benzyl, 1-naphthyl, 2-naphthyl, 1-anthracenyl, 2-anthracenyl, 9-anthracenyl, as well as other polyaromatic rings such as indene, azulene, heptalene, indacene, acenapthlene, fluroene, phenanthrene, and further heterocyclic aromatic rings such as pyridine, dihydropyridine, pyridazine, pyrmidine, pyrazine, indole, purine, indolizine, quinoline, isoquinoline, quinazoline, carbazole, phenazine, phenothiazine, and phenathridine.

Use of Peripheral Antinociceptive Pharmacophore-Compounds in Clinical Disorders

Treatment of Pain. Without being bound by theory, I believe that the peripheral antinociceptive pharmacophore compounds described here act on small sensory nerve fibers to inhibit, counteract, mask, attenuate or otherwise reduce the activation, transmission, or integration of the neuronal signal for somatic, visceral and neuropathic pain. The resulting antinociceptive effect has therapeutic benefit and relies upon adequate delivery of pharmacophore to the biological target.

Treatment of Lower Urinary Tract Disorders. The rationale is that by targeting transient receptor potential (TRP) receptors in C and Aδ sensory nerves and epithelium in the bladder and ureter, the hyper-reflexia of overactive bladder and urinary incontinence is obtunded. The presence of these receptors have been shown (Birder et al. Vanilloid receptor expression suggests a sensory role for urinary bladder epithelial cells. Proc Natl Acad Sci 2001 November 98:13396-401. Stein et al. Cool (TRPM8) and hot (TRPV1) receptors in the bladder and male genital tract. J Urol. 2004 September 72:1175-8).

Treatment of Bowel Dysfunction. Without being limited to theory I believe that peripheral antinociceptive pharmacophore-compounds here described can counteract the pain and discomforts of gut discomfort and inflammation. These compounds may be a new category of antinociceptive agents, designed to reduce intestinal perception of noxious signals by blocking the afferent nerve receptors. I postulate that these actions are therapeutically useful for treating the symptoms of enteritis, colitis, and proctitis, caused by conditions such as irritable bowel disease, irritable bowel syndrome, the side-effects of prostate brachytherapy, and other forms of gastrointestinal dysfunction.

Treatment of Obstructive Breathing Disorders and Other Noxious Sensory Disorders.

The sensory nerves that mediate the sensations of breathing disorders are also the target of the drugs of this invention; the therapeutic goal of the compounds administered being to provide refreshed breathing, less sneezing and throat irritation, less cough, decreased inspiratory effort, and relief of dyspnea.

Other noxious sensory disorders treatable with compounds of this invention include, but are not limited to, heat exhaustion, the flushing sensations of menopause, the pain of burned, traumatized or inflamed skin, itching (pruritus), and fatigue.

Bioassays For Peripheral Antinociceptive Pharmacophore-Compounds

Screening for antinociceptive activities. The "psychic adjuncts of pain" cannot be expressed by animals, that is, animals cannot say "ouch", so antinociceptive effects are inferred from inhibition of a motor withdrawal response to noxious stimuli. A standard test is the effects of the test compound on acetic acid (10 ml/kg of body weight of 0.6% in water), phenylbenzoquinone (0.02%), or $MgSO_4$ (120 mg/kg)-induced abdominal constrictor (stretch) response in mice, injected intraperitoneally with these irritants. The number of stretches is counted over a 20 min period, after injection of the test substance (n=10/group). An antinociceptive agent will decrease the frequency of stretching in a dose-dependent manner.

In humans, screening for the antinociceptive properties of peripheral antinociceptive pharmacophore-compounds may be obtained by applying a test solution (e.g. from 1 to 20 mg/ml) onto a injured skin surface, such as caused deliberately by a blister, by application of cantharidin, or by a first degree burn (Keele, C. A. and Armstrong, D. Mediators of pain, In: Pharmacology of Pain, Ed. by Lim, R. K. S. et al. pg. 3-24.1968; J. L. Pedersen Inflammatory pain in experimental burns in man. Danish Med Bull. 2000 47:168-95). Pain at the blister may be further induced by heat, or topical application of bradykinin or capsaicin. Pretreatment or post-application of the test compounds can be evaluated by questioning the test subject. The degree of pain is quantified on a visual analog scale of 1 to 10 points, with 10 being unbearably painful. Other tests on sensory thresholds are on taste, smell and thermosensation.

Bioassay of Visceral Hypersensitivity in Intestine and Bladder. The guinea pig ileum preparation is a standard pharmacological assay for measuring drug effects on the enteric nervous system and intestinal smooth muscle. Briefly, male guinea pigs are sacrificed by exposure to carbon dioxide and 15 to 20 cm segments of the ileum are removed. The intestine is then placed in Krebs-Henseleit buffer, gassed with oxygen:carbon dioxide (95:5), and maintained at 37° C. Longitudinal strips of muscle are maintained under tension and the force of spontaneous or stimulated contractions measured with a strain gauge tension transducer attached to a polygraph recorder. Contractions can be induced by electrical field stimulation or chemical mediators such as substance P, barium chloride, histamine, bradykinin, acetylcholine or serotonin and the IC50 (inhibitory concentrations) calculated for candidate peripheral antinociceptive pharmacophore-compounds. This test is standardized to compare potencies of different analogs, and the goal is to identify compounds that are inhibitory at solubilized concentrations of about 1 to 10 µM or less.

Similar methods of measuring smooth muscle contractions may be used with strips of bladder (detrusor) muscle preparations. An organ bath assay is used to test the effects of candidate drugs on the contractility of the bladder detrusor. Young adult Wistar rats (10 week old) are euthanized with carbon dioxide. The urinary bladder is excised and placed in oxygenated isotonic solution (pH 7.4). Isometric tension is recorded under an appropriate load using longitudinal strips of detrusor muscle. Bladder strips are equilibrated for 60 min before stimulation. Contractile response to 80 mM KCl is determined at 15 min intervals until reproducible responses are obtained. The response to KCl is used as an internal standard to evaluate the effect of test compounds. The effects of the compounds are investigated by incubating the strips with compounds for 30 min prior to the stimulation with an appropriate agonist or electrical stimulation. The IC50 is then calculated.

Micturition parameters, using cystometry, are utilized to evaluate the drug candidates for urinary tract disorders. Sprague-Dawley rats are anesthetized by intraperitoneal administration of sodium pentobarbital 60 mg/kg. The abdomen is opened through a midline incision, and a polyethylene catheter is implanted into the bladder through the dome. In parallel, the inguinal region is incised, and a heparinized saline polyethylene catheter is inserted into a common iliac artery. The bladder catheter is connected via T-tube to a pressure transducer and a microinjection pump. Saline is infused at room temperature into the bladder at a rate of 2.5 ml/hr with a Harvard infusion pump.

Intravesical pressure is recorded continuously on a chart pen recorder. At least three reproducible micturition cycles for baseline values are recorded before a test compound is administered. A test compound dissolved in an appropriate vehicle is injected into the arterial catheter 2 min before another administration of stimulant such as bradykinin, histamine, or capsaicin. The relative decrease in the induced intravesical pressure are analyzed from the cystometric data in comparison with the normal micturition patterns. The testing compounds-mediated inhibition of the increased bladder pressures is evaluated using Student's t-test. A probability level less than 5% is accepted as a significant difference.

The method of Luel P. et al. (Experimental bladder instability following bladder outlet obstruction in the female rat. J. Urol. 160: 2253-2257, 1998) is used for testing the effects of drug on the Lower Urinary Tract Syndrome, after bladder outlet obstruction. Wistar rats are anesthetized with ketamine, administered intraperitoneally, and the abdomen is opened via a midline incision and the bladder and the proximal urethra are exposed. To obtain a precise partial obstruction of the urethra, a catheter with an outer diameter of 1 mm is inserted a ligature is tied around the urethra. In sham-operated controls, the urethra is not manipulated. After surgery, the abdominal well is closed and the animals allowed to recover. After 6 weeks, the rats are anesthetized with ketamine and the ligature around the urethra carefully removed. A polyethylene catheter is implanted in the bladder through the dome, and exteriorized at the scapular level. Animals are then allowed to recover for at least 48 hours. Bladder pressure was measured via the T-tube two days using a strain gauge device. Un-anesthetized rats were placed in a restraing device, and using a microinjection pump warm saline was infused into the bladder at a rate of 3 ml/hr for control and obstructed animals. Overactivity of the obstructed bladders was reflected in parameters such as basal pressure, peak micturition pressure, threshold pressure, micturition interval, amplitude and frequency of spontaneous activity and micturition slope between non-ligated and ligated rats. The relative effectiveness of drug candidates are then evaluated in both groups. A significant reduction in excess excursions of bladder pressure in the overactive group provided evidence of antinociceptive suppression of excess bladder tone.

Neurophysiological and Molecular Mechanisms of Drug Action. The procedures described previously are used in drug screening. Experimentally there are additional methods to identify peripheral antinociceptive pharmacophore-compounds on sensory nerve endings. TRP receptors are present in sensory neurons. At the molecular level, the interactions of these peripheral antinociceptive pharmacophore-compounds with various TRP receptors can be characterized. The methods for such receptor studies were described by Laus et al. (Prostate tumor nucleotide compositions and methods of detection thereof. U.S. Pat. No. 6,194,152 B1, Feb. 27, 2001), and by Bevan et al. (Vanilloid receptor-related nucleic acids and polypeptides. U.S. 2003/0157633 A1, Aug. 21, 2003) and Julius et al. (Methods of modulating cold sensory perception. U.S. 2003/0219834 A1, Nov. 27, 2003), herein incorporated by reference. In the patent by Laus et al. it is noted that activation of trp-p8 by specific agonists of this receptor may also be utilized for the treatment of prostate disorders such prostate neoplasia. The use of peripheral antinociceptive pharmacophore-compounds of this discovery for prostate disorders is also contemplated in the present patent application.

Identification of Pharmacophore. The pharmacophore precursor unit of Formulas 1 and 2 was characterized based on the following measures of taste thresholds for menthol in human subjects, as shown in the data of Table 3 and 4. Based on this information, the pharmacophore precursor was selected and then the -ZR" moiety was placed on the molecule to form the peripheral antinociceptive pharmacophore compounds of this discovery with desired pharmacokinetics and adequate delivery of pharmacophore to the target.

To illustrate the use of the -Z-R" moiety for drug delivery, I will first use the case where -Z-R" is $—SO_2—R"$. A wide variety of sulfonamide antibiotics, known to the art, are obtained by $N_1$ substitution and have undergone extensive testing in human subjects. For these compounds, the $N_1$ substitution may be acyclic, such as sulfacetamide, or heterocyclic derivatives with a five-membered ring (-oxazole, -oxathiazole) such as sulfaethiazole, sulfafurazole, sulfamethizole, or sulfisoxazole, or a six-membered ring (pyridine, pyrimidine, pyrdiazine, pyrazine, or triazine ring) such as sulfapyridine, sulfadiazine, or sulfisomidine. The 5- and 6-membered heterocyclic rings may, in turn, be singly or di-methylated, or singly or di-methoxylated. After administration and absorption, the heterocyclic ring in some compounds is hydroxylated by liver enzymes. The hydroxyl group is further conjugated to the glucuronide or acetylated. The hydroxylated derivatives show less protein binding than the parent, and are cleared by the renal tubules, with active tubular secretion in some instances. The water-soluble products are then excreted. The aromatic ring of the sulfonamide may also be hydroxylated, but this occurs to a lesser extent.

A comprehensive set of data on the pharmacokinetic behavior of sulfonamide antibiotics was compiled (T. B. Vree: Pharmacokinetics of sulfonamides revisited. Basel, New York: Karger, Antibiotics and Chemotherapy; vol. 34 1985 and T. B. Vree. Clinical pharmacokinetics of sulfonamides and their metabolities: an encyclopedia. Antibiotics and Chemotherapy; v. 37). Sulfonamides was classified as ultrashort acting, short-acting, medium long-acting, long-acting and ultralong-acting with respective plasma half-lives $T_{1/2}$ of <4 hr, 4 to 8, 8 to 16, 16 to 60 and >60 hours. Examples in each category were then selected for illustration from the group of sulfachloropyridazine, sulfaclomide, sulfacytine, sulfadiazine, sulfadimethoxine, sulfadimidine, sulfadoxine, sulfaethidole, sulfaethylpyrazone, sulfafenazole, sulfafurazole, sulfaguanidine, sulfaguanol, sulf(a)iodizole, sulf(a)isomidine, sulfalene, sulfamerazine, sulfamethizole, sulfamethomidine, sulfamethoxazole, sulfamethoxydiazine, sulfamethoxypyridazine, sulfamethylthiazole, sulfametrole, sulfamonomethoxine, sulfamoxole, sulfanilamide, sulfaperine, sulfapyridine, sulfaquinoxaline, sulfaomizole, sulfasymazine, sulfathiazole, and sulfatroxazole.

The use of a $—SO_2—R"$ group to modify absorption, distribution, metabolism and excretion of a pharmacophore, and to enable delivery to a sensory neuron target, is a novel concept. Sulfonyl groups are present in many drugs, such as tolbutamide (anti-diabetic drug that releases insulin), sumatriptan (anti-migraine drug), Vioxx® and Celebrex® (selective $COX_2$-inhibitors), thiazide diuretics, and sulfasalazine (for IBD) and have a relatively good safety profile. Similarly, -Z-R" may be replaced by $—CO_2—R"$. For this category, the esters are of special interest because of the extensive database on —R" groups that are susceptible to esterases. Thus, the choice of $—O—CH_2—CH_3$ for-R" optimizes the plasma half at about 3.5 hours. A longer half-life made be obtained using a tert-butyl ester. Additional examples of drugs designed for delivery to the upper airways, the bladder/ureter, the lower intestinal lining, and the systemic circulation are shown in Formulae 4 to 6.

TABLE 3

Sensory Thresholds for Various N-substituted phenyl-alkyl and cycloalkyl carboxamides screened as pharmacophore unit precursors.

| CHEMICAL | Cold Sensation Threshold on Tongue*, μg |
|---|---|
| N-(3'-hydroxy-4'-methylphenyl)-2-isopropyl-5-methylcyclohexanecarboxamide | 0.1 |
| N-(4'-methoxyphenyl)-2-isopropyl-5-methylcyclohexanecarboxamide | 0.1 |
| N-(2',4'-dimethylphenyl)-2-isopropyl-5-methylcyclohexanecarboxamide | 0.1 |
| N-(4'-methoxy-2'-methylphenyl)-1-isopropylcycloheptanecarboxamide | 0.2 |
| N-(4'-methylphenyl)-2-isopropyl-5-methylcyclohexanecarboxamide | 0.3 |
| N-(4'-nitrophenyl)-2-isopropyl-5-methylcyclohexanecarboxamide | 0.3 |
| N-(2'-hydroxyphenyl)-2-isopropyl-5-methylcyclohexanecarboxamide | 0.5 |
| N-(4'-fluorophenyl)-2-isopropyl-5-methylcyclohexanecarboxamide | 0.5 |
| N-(4'-methoxyphenyl)-2-isopropyl-2,3-dimethylbutyramide | 0.5 |
| N-(3'-hydroxy-4'-methylphenyl)-1-isopropylcycloheptanecarboxamide | 1 |
| N-(2'-methyl-4'-methoxyphenyl)-3-n-butylbicyclo[2.2.1]hept-5-ene-2-carboxamide | 1 |
| N-(2',4'-dimethoxyphenyl)-3-isobutylbicyclo[2.2.1]hept-5-ene-2-carboxamide | 1 |
| N-(4'-hydroxyphenyl)-2-isopropyl-5-methylcyclohexanecarboxamide | 1 |
| N-(2',4'-dimethylphenyl)-2-isopropyl-2,3-dimethylbutyramide | 1 |

TABLE 3-continued

Sensory Thresholds for Various N-substituted phenyl-alkyl and cycloalkyl carboxamides screened as pharmacophore unit precursors.

| CHEMICAL | Cold Sensation Threshold on Tongue*, μg |
|---|---|
| N-(2'-methyl-4'-methoxyphenyl)-3-isobutylbicyclo[2.2.1]hept-5-ene-2-carboxamide | 1 |
| N-(4'-acetylphenyl)-2-isopropyl-5-methylcyclohexanecarboxamide | 2 |
| N-(4'-methoxyphenyl)-2-isopropyl-2,4-dimethylpentanamide | 2 |
| N-(4'-methylphenyl)-2-isopropyl-5-methylcyclohexanecarboxamide | 3 |
| N-(3',4'-dimethylphenyl)-2-isopropyl-2,3-dimethylbutyramide | 3 |
| N-(4'-methoxyphenyl)-3-isobutylbicyclo[2.2.1]hept-5-ene-2-carboxamide | 4 |
| N-(3'-hydroxy-4'-methoxyphenyl)-3-n-butylbicyclo[2.2.1]hept-5-ene-2-carboxamide | 5 |
| N-(3',4'-dimethoxyphenyl)-1-isopropylcycloheptanecarboxamide | 5 |
| N-(4'-ethoxycarbonylphenyl)-2-isopropyl-5-methylcyclohexanecarboxamide | 5 |
| N-(2',5'-dimethylphenyl)-2-isopropyl-2,4-dimethylpentanamide | 5 |
| N-(4'-methoxyphenyl)-1-ethyl-2-methylcycloheptanecarboxamide | 6 |
| N-(1'-naphthyl)-2-isopropyl-5-methylcyclohexanecarboxamide | 6 |
| N-(3'-hydroxy-4'-methoxyphenyl)-3-isobutylbicyclo[2.2.1]hept-5-ene-2-carboxamide | 8 |
| N-(4'-methoxyphenyl)-1,7,7-trimethylbicyclo[2.2.1]heptane-2-carboxamide | 8 |
| N-(4'-chlorophenyl)-2-isopropyl-5-methylcyclohexanecarboxamide | 8 |
| N-(3'-hydroxyphenyl)-1-isopropylcycloheptanecarboxamide | 10 |
| N-(2',4'-dimethylphenyl)-1-isopropylcycloheptanecarboxamide | 15 |
| N-(3',4'-dimethylphenyl)-1-isopropylcycloheptanecarboxamide | 15 |
| N-(4'-methoxyphenyl)-3-isopropylbicyclo[2.2.1]heptane-2-carboxamide | 15 |
| N-(4'-methoxyphenyl)-3,3-dimethylbicyclo[2.2.1]heptane-2-carboxamide | 20 |
| N-(2',5'-dimethylphenyl)-3,3-dimethylbicyclo[2.2.1]heptane-2-carboxamide | 20 |
| N-phenyl-2-isopropyl-5-methylcyclohexanecarboxamide | 20 |
| N-phenylmethyl-2-isopropyl-5-methylcyclohexanecarboxamide | 20 |

*Filter paper (1 × 1 cm) was impregnated with a known amount of compound and placed on the tongue of the test subject. After 30 sec, the subject was required only to report presence or absence of a cooling effect. Individual sensitivity varied over a considerable range; for example, for 23 subjects, chosen at random, the threshold for a standard such as menthol ranged from 0.02 to 10 μg. Ethoxycarbonyl is —(O═C)—O—CH$_2$H$_5$.

TABLE 4

Threshold Cooling Effect of p-menthane carboxylic acid esters

| p-menthane-COOR where HO-R is the alcohol | chemical structure (R) | μg |
|---|---|---|
| diethylene glycol | —CH2CH$_2$OCH$_2$CH$_2$OH | 1 |
| glycerol | —CH$_2$CH(OH)CH$_2$OH | 1.2 |
| propylene glycol | —CH$_2$CH(CH$_3$)CH$_2$OH/—CH$_2$CH(OH)CH$_3$ isomeric mixture | 1.4 |
| ethylene glycol | —CH$_2$CH$_2$OH | 1.5 |
| butan-2,3-diol | —CH(CH$_3$)CH(CH$_3$)OH | 3 |
| cyclohexan-1,2-diol | —CH(OH)CH(OH)[CH$_2$]$_4$ | 4 |
| triethylene glycol | —CH$_2$CH$_2$(OCH$_2$CH$_2$)$_2$OH | 5 |
| butyn-1,4-diol | —CH$_2$C≡CCH$_2$OH | 6 |
| propan-1,3-diol | —CH$_2$CH$_2$CH$_2$OH | 7 |
| hexylene glycol | —CH$_2$CH(OH)CH$_2$CH$_2$CH$_2$CH$_3$/—CH$_2$CH$_2$CH$_2$CH$_3$)CH$_2$OH isomeric mixture | 8 |
| lactic acid | —CH(CH$_3$)COOH | 8 |
| 2,2-dimethyl-4-hydroxymethyl-1,3-dioxolan | —CH$_2$CH(-)CH$_2$OC(CH$_3$)$_2$O— | 11 |
| butan-1,4-diol | —CH$_2$CH$_2$CH$_2$CH$_2$OH | 12 |
| 3,5-dihydroxytoluene | —C$_6$H$_3$(CH$_3$)(OH) | 15 |
| glycollic acid | —CH$_2$COOH | 15 |
| 2-hydroxy-2-methylpropanoic acid | —C(CH$_3$)$_2$COOH | 20 |
| 2-acetoxoyethanol | —CH$_2$CH$_2$OCOCH$_3$ | 33 |
| sorbitol | —CH$_2$CH(OH)CH(OH)CH(OH)CH(OH)CH$_2$OH | 50 |
| ethyl lactate | —CH(CH$_3$)COOC$_2$H$_5$ | 50 |

TABLE 4-continued

Threshold Cooling Effect of p-menthane carboxylic acid esters

| p-menthane-COOR where HO-R is the alcohol | chemical structure (R) | μg |

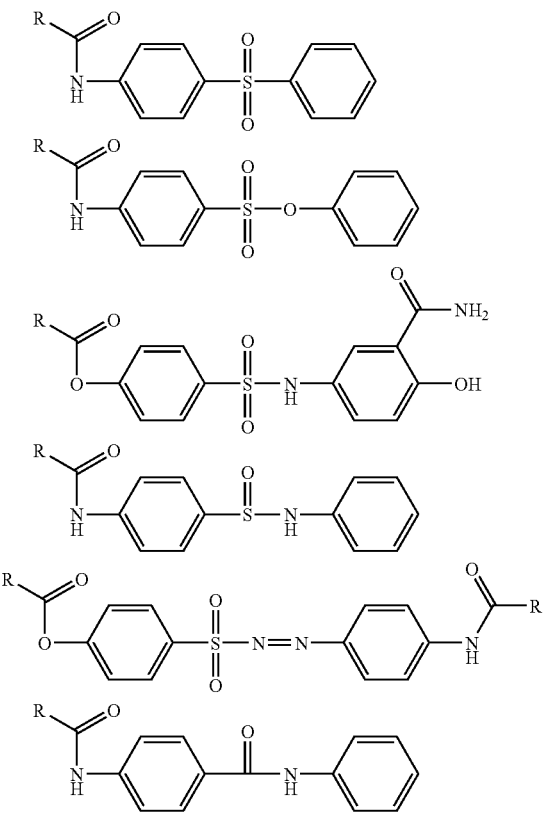

[d] 2-sec-Butyl-3-methyl-pentanoic acid (4-tert-butylsul-famoyl-phenyl)-amide

[e] 2-Isopropyl-5-methyl-cyclohexanecarboxylic acid [4-(pyrimidin-2-ylsulfamoyl)-phenyl]-amide

[f] 4-[(2-Isopropyl-5-methyl-cyclohexanecarbonyl)-amino]-N-pyrimidin-2-yl-benzamide Formulae 5(a-f). Embodiments for Lower Bowel Disorders (clockwise from top left panel). For branched aliphatics, the -R attached to the carbonyl carbon is, for example, to the "3" position of 2,3,4-trimethyl-pentane and 2,4-dimethyl-hexane, and to the "4" position of 3,5-dimethyl-heptane. For cycloalkyls, examples of —R are: 1-isopropylcycloheptyl, 1-isopropylcyclohexyl, 1-isopropyl-2-methylcyclohexyl, 1-isopropyl-2-methylcyclopentyl; 2-isopropyl-5-methylcyclohexyl (p-menthyl), 3-isopropyl-bicyclo[2.2.1]hept-2-yl; and 3-isobutyl-bicyclo[2.2.1]hept-5-en-2-yl.

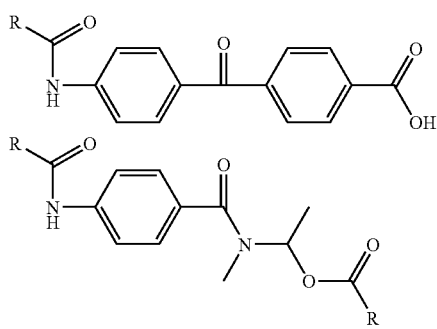

Formulae 4(a-f). Antinociception and Lower Urinary Tract Disorder embodiments (clockwise from top left panel):

[a] 2-Isopropyl-5-methyl-cyclohexanecarboxylic acid (4-acetylsulfamoyl-phenyl)-amide.

[b] 4-(1-Isopropyl-2-methyl-cyclopentanecarbonyloxy)-benzoic acid ethyl ester,

[c] 1-Isopropyl-cycloheptanecarboxylic acid [4-(diethyl-carbamoyl)-phenyl]-amide

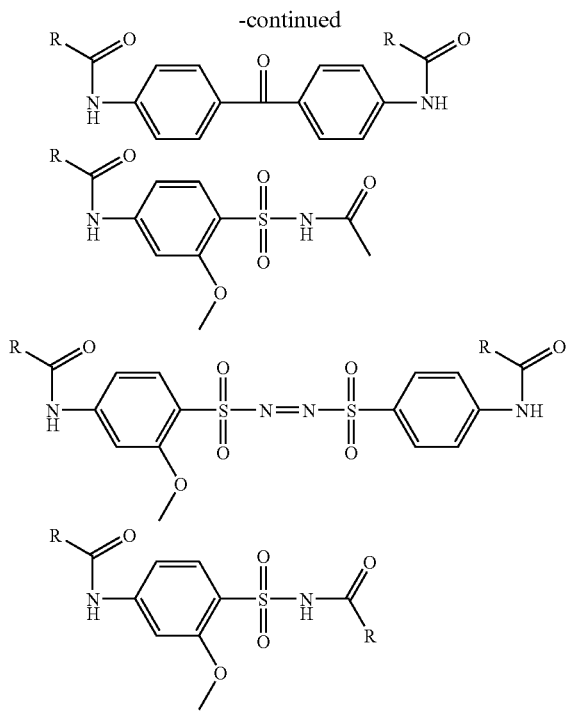

Formulae 6(a-f). Additional Embodiments (clockwise beginning with the top left panel):
(a) Agent for lower urinary tract,
(b) Agent for systemic antinociception,
(c) Agent for high penetrance into body tissues, e.g. synovial fluid for osteoarthritis,
(d) Agent for longterm system antinociception,
(e) Agent for release in the lower bowel,
(f) Agent for use as insect repellent.

For branched aliphatics, the —R attached to the carbonyl carbon is, for example, to the "3" position of 2,3,4-trimethylpentane and 2,4-dimethyl-hexane, and to the "4" position of 3,5-dimethyl-heptane. For cycloalkyls, examples of —R are: 1-isopropylcycloheptyl, 1-isopropylcyclohexyl, 1-isopropyl-2-methylcyclohexyl, 1-isopropyl-2-methylcyclopentyl; 2-isopropyl-5-methylcyclohexyl (p-menthyl), 3-isopropyl-bicyclo[2.2.1]hept-2-yl; and 3-isobutyl-bicyclo[2.2.1]hept-5-en-2-yl.

Delivery to Target and Therapeutic Applications of Peripheral Antinociceptive Pharmacophore Embodiments In practicing this discovery the peripheral antinociceptive pharmacophore compounds, applied topically to inflamed skin and mucous membranes, will typically relieve itch, irritation and pain. By "topical" is meant application onto surfaces of the body in contact with air, which includes the skin, the eye surface, the upper and lower respiratory tract, and the entrance and exit of the gastrointestinal tract, that is, the oral cavity and the anorectum. Suitable topical formulations, for example, include compositions such as powders, pastes, lotions, liniments, creams and ointments, nasal and throat drops, aerosols and sprays, dentifrice (toothpaste), chewing gum, mouthwash and gargle compositions. Topical products, in this context, also include articles such as bandages, suppositories, cleansing tissues, cosmetics, and toothpicks. Metered nasal and throat sprays of CPS-125 are especially attractive as a product for breathing disorders because of its long-lasting cooling and refreshing actions in the nasal and oral cavities (see example). Examples of metered dose dispensers currently used for drug delivery are Nasarel® and Flonase®.

In formulating topical compositions to practice this discovery, the peripheral antinociceptive pharmacophore compound may be incorporated into a vehicle that by itself may be inert or may contain other active ingredients (e.g. a glucocorticosteroid). A wide variety of vehicles will be suitable, depending upon the particular product involved, such vehicles including solids, liquids, emulsions, foams and gels. Typical vehicles include aqueous or alcoholic solutions, oils and fats such as hydrocarbon oils, fatty acid esters, long chain alcohols and silicone oils; phospholipid micelles such liposomes, using micro- or nano-technologies; as finely divided solids such as starch or talc; cellulosic materials such as paper tissue; low-boiling hydrocarbons; gums and natural or synthetic resins. For applications to the ocular surface or to the upper or lower respiratory tract, the compound may be packaged in unit dose dispensers.

Therapeutic indications for which a topical formulation may be beneficial include pain and itch from the skin, as occurs in various forms of dermatitis (atopic, contact and irritant); pain from burned, traumatized or irritated skin; from procedures related to wound debridement; itch and discomfort from insect bites; itch and pain from skin infections, sunburn, actinic keratoses, basal cell carcinoma; pruritus due to xerosis; cheilitis or itching of the lips from cold sores. Other topical surfaces include pain in the entrance of the gastrointestinal tract that can occur from conditions such as mucositis, apthous ulcers, etc. Pain and itch in the exit occur in pruritus ani, hemorrhoids, anal fissures, anal fistulas, after hemorrhoidectomy, perineal inflammation, anogenital skin inflammation and various local causes such as incontinence, diaper rashes, etc. For mucous membranes itch and pain is common in the vulva (e.g. from candidiasis), in the vaginal wall (e.g. vestibulitis and vulvodynia), dyspareunia, and anogenital infections, including warts and sexually transmitted diseases, and viral infections (especially in immunocompromised patients). In the nostrils, nasal membranes, or upper always sensations are frequently perceived as obstructed breathing, e.g. associated with congestion, rhinitis, asthma, bronchitis, emphysema and chronic obstructive pulmonary diseases, sleep apnea and snoring. Finally, itch and pain also originate from the eye surface, e.g. conjunctivitis, pain from corneal abrasions, and pain from eye surgery. All of these conditions can be relieved by a peripheral antinociceptive pharmacophore.

The effective amount of peripheral antinociceptive pharmacophore compound can also be administered to the lining of the esophagus and stomach with a fast-dissolving or a simple gelatin coated capsule. Alternatively, the target of the colon of a patient may be reached by oral ingestion of a unit dosage form such as an enterically coated capsule such that the compound is released in the lining of the lower intestinal tract, e.g., in the disal ileum and in the colon of the patient. The enteric-coated capsule, designed to avoid upper gastrointestinal absorption, is a method well-known to practioners of the art. A preferred unit dose is wherein peripheral antinociceptive pharmacophore-compound is present in an amount of about 10 mg to about 1000 mg per capsule. Enteric coatings remain intact in the stomach, but will dissolve and release the contents of the dosage form once it reaches the region where the pH is optimal for dissolution of the coating used. The purpose of an enteric coating is to substantially delay the release of the peripheral antinociceptive pharmacophore-compound until it reaches its target site of action in the ileum or colon. Aqueous film-coating technology is employed for the enteric coating of pharmaceutical dosage forms. Delayed-released oral dosage forms, including osmotic minipump delivery formulations, have the potential advantage of delivering nearly all the peripheral antinociceptive pharmacophore-compound to the ileum or colon in an easily administered form.

If the target is to be reached via the bloodstream, an oral formulation is designed to be optimally absorbed from the gastrointestinal tract and to achieve steady blood or plasma levels. Here again, a simple gelatin capsule or an enteric coated pill or capsule, designed for optimum dissolution at a given pH, is a familiar formulation to practitioners skilled in the art. Extensively used chemicals for enteric coating are cellulose acetate phthalate, methacrylic acid ester copolymers with acidic ionizable groups, and polyvinyl acetate phthalate. Standard coating ingredients are widely sold under the trademark of Eudragit® (Degussa Chemicals, Inc.). Dosage forms coated with methacrylic acid polymers dissolve in the ileum at about pH 6.8, and in the terminal ileum and caecum at about pH 7.2. In general coating thicknesses of about 25 to 200 microns, and especially 75 to 150 microns, are preferred using about 3 to 25 mg, preferably 8 to 15 mg of acidic coating material per square centimer of tablet or capsule surface. The precise coating thickness will however depend upon the solubility characteristics of the material used and the site to be treated.

The peripheral antinociceptive pharmacophore compounds and compositions described here have the desirable properties of non-irritancy and safety. For example, the embodiment called CPS-125 is a conjugate of WS-3, a food additive p-menthoyl-carboxamide that is Generally Recognized As Safe (GRAS), and sulfiazine, a familiar antibiotic. The silver salt of sulfadiazine is applied topically at 3 to 5 mm thickness, in 50 g packets, for the treatment of burn wounds. Sulfadiazine is given at doses of 1 to 2 g administered four times a day for 6 to 8 weeks in the treatment of acute Toxoplasma encephalitis in HIV-infected patients. Lower doses of sulfadiazine are used for urinary tract infections.

Therapeutic or recreational uses of an oral formulation containing the inventive embodiments, alone or in combination with another pharmaceutical agent, would include conditions such as heat exhaustion and fatigue, nasal and eye irritation, obstructed breathing disorders, lower urinary tract disorders, heartburn, irritable bowel disease or the irritable bowel syndrome, pruritus, and systemic pain.

Synthesis of Peripheral Antinociceptive Pharmacophore Compounds of this Discovery Branched chain alkyl carboxamides are available from commercial sources, or are synthesised by standard methods known to the art. Likewise, p-menthane carboxylic acid is readily prepared by carbonation of Grignard reagent derived from 3-chloro-p-menthane (obtained by reaction menthol with zinc chloride in hydrochloric acid). The carboxylic acid, oriented in the equatorial axis relative to the carbonyl carbon, is then converted into its acid chloride, for example, by reaction with thionyl chloride. The acid chloride is then reacted with the amino moiety of a substituted aniline.

For example, in the case where the reactant with p-menthoyl chloride is a sulfanilamide, the sulfinilamide may be available commercially or methods of synthesis are known to those skilled in the art. For example, sulfacetanide, sulfadiazine, sulfanilamide, sulfisomidine and sulfathiazole are listed and can be purchased from the catalog of Aldrich Co., St. Louis, Mo. To synthesize the candidate peripheral antinociceptive pharmacophore compound, the aniline is usually dissolved in a suitable solvent (e.g. dry tetrahydorfuran) in the presence of a suitable non-nucleophilic proton acceptor, such as triethylamine. Then, the reactants are stirred, with adjustment of reaction temperature as necessary by external heat or by cooling. On completion of the reaction, as evidenced by the disappearance of the carbonyl stretching absorption of the acid chloride from the infra-red spectrum, the mixture is then washed with dilute hydrochloric acid or sulfuric acid to remove excess amine, and then washed with dilute sodium hydroxide to remove unreacted acid chloride and any p-menthane-3-carboxylic acid, before being washed with distilled water and dried over a suitable dying agent. The solvent is removed by evaporation and the crude product re-crystallised from a suitable solvent or solvent mixture. The confirmation of purity and identity is by standard chromatography and mass spectrometry analysis. Further description of methods of synthesis are in the Examples, which are intended to illustrate, but not to limit, this discovery.

EXAMPLE 1

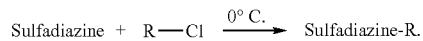

0.79 ml (0.0039 mol) of p-menthoyl chloride (R—Cl) dissolved in 7 ml of dry acetone was added dropwise to a stirred solution of 1.1 g (0.0039 mol) sulfadiazine in 10 ml of dry pyridine keeping the temperature at 0° C. After addition of sulfadiazine was complete, stirring at 0° C. was continued for 10 min and then, at room temperature for 60 min.

The solution was evaporated. The oily residue dissolved in EtOAc was washed with 5% $NaHCO_3$, water and dried over anhydrous $Na_2SO_4$. Then EtOAc was evaporated and oily residue was crystallized with $Et_2O$.

Yield: 1.102 g. (63%).

EXAMPLE 2

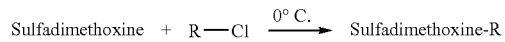

1,2 ml (0,0059 mol) of p-menthoyl chloride (R—Cl) dissolved in 9 ml of dry acetone was added dropwise to a stirred solution of 1.82 g (0.0059 mol) sulfadimethoxine in 20 ml of dry pyridine keeping the temperature at 0° C. After addition of sulfadimethoxine was complete, stirring at 0° C. continued for 10 min and then, at room temperature for 60 min.

The solution was evaporated. The oily residue dissolved in EtOAc was washed with 5% $NaHCO_3$, water and dried over anhydrous $Na_2SO_4$. Then EtOAc was evaporated and oily residue was crystallized with $Et_2O$.

Yield: 1.95 g. (69,9%).

EXAMPLE 3

Sulfonamides are used as topical and systemic antibiotics. Generally, these drugs are used at doses of 500 mg to gram quantities, and have relatively low toxic side effects except for the risks of renal crystalluria and drug hypersensitivity reactions. Seven sulfonamide compounds (sulfadiazine, sulfanilamide, sulfadimethoxine, sulfisoxazole, sulfameter and sulfamethoxypyridazine) were obtained from Sigma-Aldrich Corp. (St. Louis, Mo.) and coupled to p-menthoyl chloride, using the chemical synthesis described above. Each compound was then tested at 20 mg/ml on the lips and nasal mucous membranes. The compounds were added to sterile saline-10% Tween 80 mixture and stirred using a glass rod until the mixture was a homogeneous suspension. Using a clean glass rod, the suspension was first applied to the lips and nasal vestibule. After this trial, a dropper was used to apply the suspension into the nostrils, at a volume of 0.06 ml in 2 droplets per nostril. A gentle, cooling refreshing effect was obtained, on the lips and on breathing sensation, lasting up to 3 hr after application of 1 mg per nostril, especially with the sulfadiazine analog, coded as CPS-125. The sulfanilamide analog was inactive, the sulfadimethoxine, sulfisoxazole analogs were slightly active, and the sulfameter and sulfamethoxypyridazine analogs had moderate activities.

EXAMPLE 4

Human embryonic kidney cells were transiently transfected with the gene for the mouse TRP-M8 receptor. These cells were then voltage patch-clamped in a standard microscopic apparatus and the test solution electronically applied for 10 sec. The integrated areas of the inward current, measured in picoAmperes were then recorded. Icilin a standard cooling antinociceptive agent was used the positive control. Test substances were applied at 1 µM to at least 4 cells and the current recorded. With the potency of icilin as 100, CPS-125 had 41% of the activity of icilin and CPS-126 (the sulfanilamide analog) had 2% of the icilin activity. Further analysis of the dose-response relationship showed the EC50 of CPS-125 for full activation of the receptor was 2 µM. These results confirm the observations made in the human experiments, and provide a neuronal mechanism for the CPS-125 structure to activate antinociceptive processes in biological systems.

EXAMPLE 5

Human embryonic kidney cells were permanently transfected with the gene for the human TRP-M8 receptor. These cells were then incubated with a calcium fluorescence indicator (Fura-2) and incubated at either 29 or 37° C. These cells were then distributed into a 96-well fluorescence-plate image reader with automated drug dilution and computerized software for dose-response analysis. The influx of calcium upon drug stimulated was quantified in fluorescence units. Icilin and menthol, standard sensory nerve agonists with antinociceptive properties, were used the positive control and gave median effective concentration activities of 0.8 and 25 µM (EC50) activities. The EC50 of CPS-125 in this test system was 6 µM and for the sulfodimethoxinyl- derivative, it was 60 µM. Other carbonyl, carbamyl, sulfonyl and sulfoamyl derivatives were less active than CPS-125, with activities ranging from 8 to 100 µM for changes in fluorescence units of greater than 1000. Further analysis of the dose-response relationship showed the ΔFmax (the maximum fluorescence increase induced by a compound at the maximum concentration tested) for CPS-125 of 14,000 units which was similar to that seen with icilin and menthol, confirming full activation of the receptor.

In sum, as illustrated by the examples, novel molecular structures are described that activate TRP-receptor mechanisms, trigger sensory processes, and produce coolness and soothing antinociceptive sensations for therapeutic applications.

I claim:

1. The compound 2-isopropyl-5-methyl-cyclohexanecarboxylic acid [4-(pyrimidin-2-ylsulfamoyl)-phenyl]-amide or pharmaceutically acceptable salts thereof.

2. A therapeutic composition, comprising:
   an amount of the compound 2-isopropyl-5-methyl-cyclohexanecarboxylic acid [4-(pyrimidin-2-ylsulfamoyl)-phenyl]-amide or a pharmaceutically acceptable salt thereof, the amount being therapeutically effective in a patient when administered topically or orally; and,
   a vehicle adapted to facilitate the administration of the compound or salt thereof.

3. The composition as in claim 2 wherein the administration is oral, and the therapeutic effectiveness is in relieving sensations of visceral discomfort.

4. The composition as in claim 2 wherein the administration is topical to inflamed skin or mucous membranes, and the therapeutic effectiveness is in relieving itch, irritation or pain.

5. The composition as in claim 2 wherein the vehicle is adapted for topical administration.

6. The composition as in claim 2 wherein the vehicle is adapted for oral administration and includes a coated capsule.

* * * * *